US009598352B2

(12) United States Patent
Lee et al.

(10) Patent No.: US 9,598,352 B2
(45) Date of Patent: Mar. 21, 2017

(54) PROCESS AND DEVICE FOR THE PRODUCTION OF POLYHEDRAL BORANES

(71) Applicant: The Curators of the University of Missouri, Columbia, MO (US)

(72) Inventors: Mark Wayne Lee, Columbia, MO (US); Marion Frederick Hawthorne, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 14/357,684

(22) PCT Filed: Nov. 16, 2012

(86) PCT No.: PCT/US2012/065495
§ 371 (c)(1),
(2) Date: May 12, 2014

(87) PCT Pub. No.: WO2013/115889
PCT Pub. Date: Aug. 8, 2013

(65) Prior Publication Data
US 2014/0378707 A1 Dec. 25, 2014

Related U.S. Application Data

(60) Provisional application No. 61/561,489, filed on Nov. 18, 2011.

(51) Int. Cl.
*C07F 5/02* (2006.01)
*C07C 211/63* (2006.01)
*C01B 35/02* (2006.01)

(52) U.S. Cl.
CPC .......... *C07C 211/63* (2013.01); *C01B 35/026* (2013.01)

(58) Field of Classification Search
CPC .................................................... C07C 211/63
See application file for complete search history.

(56) References Cited

U.S. PATENT DOCUMENTS

| | | | |
|---|---|---|---|
| 4,150,057 A | 4/1979 | Sayles | |
| 4,391,993 A | 7/1983 | Sayles | |
| 6,355,840 B1 | 3/2002 | Hawthorne | |
| 6,664,426 B1 | 12/2003 | Hawthorne | |
| 6,710,155 B2 | 3/2004 | Lemmon | |
| 6,781,005 B1 | 8/2004 | Casteel, Jr. | |
| 7,521,564 B1 | 4/2009 | Shackelford | |
| 7,524,477 B2 | 4/2009 | Spielvogel | |
| 7,718,154 B2 | 5/2010 | Ivanov et al. | |
| 2003/0114632 A1 | 6/2003 | Ortega | |
| 2005/0132640 A1 | 6/2005 | Kelly et al. | |
| 2005/0169828 A1* | 8/2005 | Spielvogel | C01B 6/10 423/294 |
| 2006/0196112 A1 | 9/2006 | Berry | |
| 2009/0118526 A1 | 5/2009 | Banavali et al. | |

FOREIGN PATENT DOCUMENTS

| | | |
|---|---|---|
| DE | 102008004530 A1 | 7/2009 |
| DE | 102008050557 A1 | 4/2010 |
| DE | 102009011308 A1 | 9/2010 |
| EP | 1624519 A1 | 2/2006 |
| EP | 1734003 A2 | 12/2006 |
| EP | 1734004 A1 | 12/2006 |
| EP | 1763099 A2 | 3/2007 |
| EP | 1930336 A1 | 6/2008 |
| EP | 2062856 A1 | 5/2009 |
| EP | 2206680 A2 | 7/2010 |
| RU | 2123474 C1 | 12/1998 |
| RU | 2005105861 A | 8/2006 |
| RU | 2357015 C1 | 5/2009 |
| RU | 2378195 C1 | 1/2010 |
| RU | 2384525 C1 | 3/2010 |
| RU | 2394840 C1 | 12/2011 |
| SU | 1695619 A1 | 7/1987 |
| WO | 97-23487 A2 | 7/1997 |
| WO | WO9912776 A1 | 3/1999 |
| WO | 99-16731 A2 | 4/1999 |
| WO | 01-27028 A1 | 4/2001 |
| WO | 02-36557 A2 | 5/2002 |
| WO | 2009-058405 A1 | 5/2009 |
| WO | 2009-058406 A1 | 5/2009 |
| WO | 2009-058408 A1 | 5/2009 |

OTHER PUBLICATIONS

Adams, Convenient Preparation of the Dodecahydrododecaborate Ion; vol. 3, No. 3, Mar. 1964; p. 461; Geneva College, Beaver Falls, Pennsylvania.
Barendt; Boron Hydrides. Heteroboranes, and Their Metalla Derivatives (Commercial Aspects); Kirk-Othmer Encyclopedia of Chemical Technology.
Colombier; Separation of M2B10H10 and M2B12H12 (M=Li or Et4N) salts by HPLC (High Performance Liquid Chromatography) on a silicagel column; May 16, 1987; Note of Laboratory.
Dunks; A Simplified Preparation of B1OH14 from NaBH4; Journal of the American Chemical Society; vol. 100, No. 8; Apr. 12, 1978; pp. 2555-2556.
Ellis; A Convenient Preparation of B12H122-Salts; Communications to the Editor; Dec. 5, 1963; p. 3885.
Ellis; Comments Regarding Borane Synthesis; Communications to the Editor; vol. 85; Dec. 5, 1963; pp. 3885-3886.
Greenwood; A Novel Synthesis of the B12H122-Anion; Department of Inorganic Chemistry, the University, Newcastle upon Tyne; Sep. 26, 1963; p. 338.
Guomin; The Study of Boron Compound; Wu Han University, Department of Chemistry.

(Continued)

*Primary Examiner* — Yong Chu
*Assistant Examiner* — Ana Z Muresan
(74) *Attorney, Agent, or Firm* — Polsinelli PC

(57) ABSTRACT

The present invention provides methods and devices for producing polyhedral boron compounds. The process is generally an anhydrous, one-pot process that comprises a pyrolytic reaction of a tetraborohydride with a quaternary amine salt to form the polyhedral borane. In another aspect of the present invention, polyhedral boranes are produced, without isolation of the Lewis base-borane complex.

20 Claims, 9 Drawing Sheets

(56) References Cited

OTHER PUBLICATIONS

Hawthorne; A Mechanism Study of B10H10-2 Formation; Communications to the Editor; Dec. 5, 1964; pp. 5338-5339.
Hill; 1,2-Dicarba-closo-Dodecaboranes: p. 37.
Klanberg; New Polyhedral Borane Anions, B9H92- and B11H112-; Inorganic Chemistry; vol. 5, No. 11; Nov. 1966; pp. 1955-1960.
Middaugh; Purification, Voltammetry, and boron-11 Nuclear Magnetic Resonance Spectra of Undecahydro-closo-undecaborate(2-) Salts; Inorganic Chemistry; vol. 10, N9. 2, 1971; pp. 423-424.
Miller; Syntheses of Polyhedral Boranes; Inorganic Chemistry; vol. 3, No. 10; Oct. 1964; pp. 1456-1463.
Oussas; Study of the synthesis of decahydrodecaborate B10H102- and dodecahydrododecaborate B12H122-ions; Mar. 20, 1984; pp. 1-5.
Pitochelli; The Isolation of the Icosahedral B12H12-2 Ion; Communications to the Editor; vol. 82: Jun. 20, 1960; pp. 3228-3229.
Volkov; Synthesis of [B10H10]2- and [B12H12]2- Anions by the Reaction of Alkali Metals Tetrahydroborates with Alkylaminoboranes; Russian Chemical Bulletin; No. 2; 1980; pp. 400-401.

* cited by examiner

SECT. B-B

PROCESS AND DEVICE FOR THE PRODUCTION OF POLYHEDRAL BORANES

CROSS REFERENCE TO RELATED APPLICATIONS

This application claims priority to U.S. Provisional Application No. 61/561,489, filed on Nov. 18, 2011, which is hereby incorporated by reference in its entirety.

GOVERNMENTAL RIGHTS

This invention was made with government support under Grant No. W15QKN-06-D-0031 TASKS 8,9,10 awarded by US Army, Picatinny Arsenal. The government has certain rights in the invention.

FIELD OF THE INVENTION

The present invention provides methods and devices for producing polyhedral boron compounds. In particular, the present invention relates to a one-pot, anhydrous pyrolysis of a quaternary amine salt with a tetraborohydride to produce the polyhedral boron compounds using a vented milling reactor device. The process is tunable to give high yields of the desired polyhedral borane, and it is suitable for large scale reactions.

BACKGROUND OF THE INVENTION

Polyhedral boranes, especially decahydrodecaborate $[B_{10}H_{10}]^{2-}$ and dodecahydrododecaborate $[B_{12}H_{12}]^{2-}$ salts are useful compounds for a variety of purposes including for propellant fuels, battery electrolytes, and as precursors to carborane compounds, which have a variety of applications in various fields including the biomedical field. Decahydrodecaborate, dodecahydrododecaborate, and carboranes are stable in air, water, and high temperatures.

Despite the utility and commercial value of polyhedral boranes, potential applications for polyhedral boranes are impeded by the difficulty of manufacturing polyhedral boranes. Existing methods of producing polyhedral boranes present a number of safety concerns. First, some methods rely on the use of toxic and difficult to handle reagents such as diborane, which can explode on contact with air. Second, the pathway to polyhedral boranes proceeds through a large number of intermediates, some of which are highly unstable and can be explosive. Further complicating the reaction, a large amount of flammable gasses, including $H_2$ gas, are produced during the reaction, so the reactions must be conducted to avoid the build up of pressure, and also to dilute the flammable gas to safe levels.

Methods have been developed to avoid the use of diborane, but these methods are low yielding. Most synthetic routes that avoid diborane require an additional isolation step for isolating a boron intermediate prior to reaction of the polyhedral borane. Additional steps are undesirable as they reduce the efficiency of the reaction. Reactions where the complex is not isolated have not proved durable and they often require expensive solvents or catalysts. Moreover, these reactions typically produce unwanted byproducts that are difficult to separate from the polyhedral boranes.

Control of the polyhedral boranes produced has been difficult in prior processes. Control to produce a high yield of a single polyhedral borane has also been difficult. Dodecahydrododecaborates have been produced through various methods but these methods have been unable to produce high levels of decahydrodecaborate, the more valuable of the two polyhedral boranes. As decahydrodecaborate and dodecahydrododecaborate are often produced together, separation must be provided for the pure products. Previous methods of separation have been labor intensive.

Therefore, there is a need for a process for producing polyhedral boranes in good yields and in a safe and efficient manner compatible with large scale production.

SUMMARY OF THE INVENTION

One aspect of the invention provides a process for the production of polyhedral boranes. The process is generally an anhydrous, one-pot process that comprises a pyrolytic reaction of a tetraborohydride with a quaternary amine salt to form the polyhedral borane. In another aspect of the present invention, polyhedral boranes are produced without isolation of the Lewis base-borane complex.

The invention also provides a device for the production of polyhedral boranes.

Other features and iterations of the disclosure are described in more detail herein.

BRIEF DESCRIPTION OF THE FIGURES

The following figures illustrate various aspects of the invention.

Figure 1:
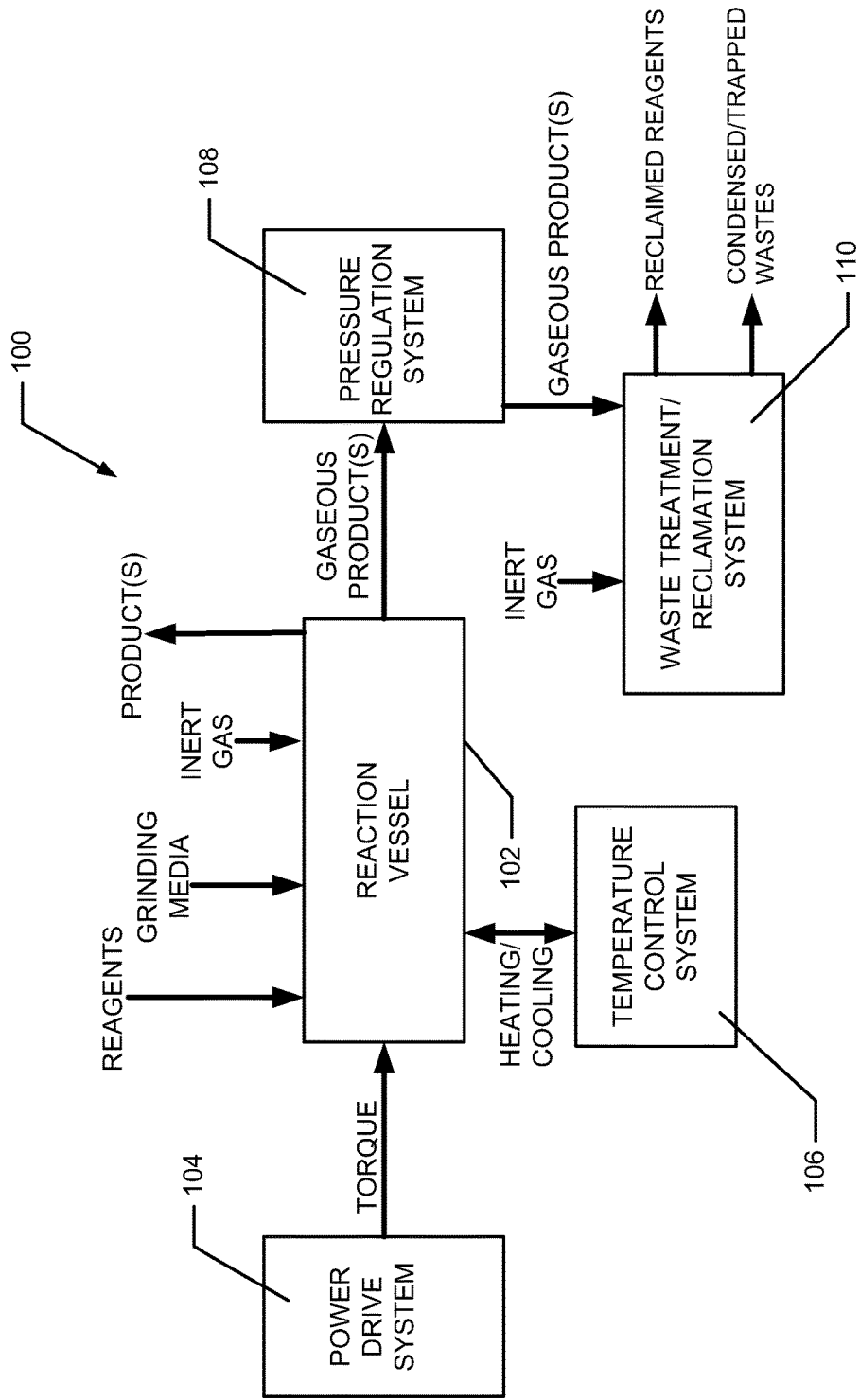
FIG. 1 is a block diagram illustrating the arrangement of subsystems of a milling reactor system.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the detailed description is to be regarded as illustrative in nature and not restrictive.

DETAILED DESCRIPTION OF THE INVENTION

Briefly, therefore, the present invention relates to an improved process for the production of polyhedral boranes. The process is generally an anhydrous, one-pot process that comprises a pyrolytic reaction of a tetraborohydride with a quaternary amine salt to form the polyhedral borane. In another aspect of the invention, polyhedral boranes are produced without isolation of a Lewis base-borane complex. Finally, a device is provided for the production of polyhedral boranes.

Synthetic methods for producing polyhedral boranes without the use of diborane reagents generally require the isolation of a Lewis base-borane complex. Lewis base-borane complexes are formed by the reaction of a borohydride reagent with a Lewis base. The resulting Lewis base-borane complex has been generally thought to facilitate the formation of polyhedral boranes without a diborane reagent. The Lewis base-boranes complexes, as an intermediate to the process, introduce atom inefficiencies, as the Lewis base is not incorporated in the final product, and generally represents an additional synthetic step, reducing the efficiency for producing polyhedral boranes.

In one embodiment, decahydrodecaborane $[B_{10}H_{10}]^{2-}$ and dodecahydrododecaborane $[B_{12}H_{12}]^{2-}$ are produced via a one-pot, anhydrous pyrolytic process. The process comprises reacting a tetraborohydride with a quaternary amine salt to give the polyhedral boranes as shown in Reaction Scheme 1 below.

Reaction Scheme 1

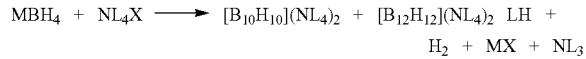

Another aspect of the invention is the production of polyhedral boranes without the isolation of a Lewis base-borane complex.

In yet another embodiment, a process for producing the polyhedral boranes in a milling reactor is provided. The reactor provides a controlled environment for the production of polyhedral boranes including control over temperature and pressure and also provides a grinding/mixing mechanism to improve the yield of the polyhedral boranes.

One aspect of the invention described herein is the scalability of the reaction. The parameters provided allow the reaction to be safely scaled to produce higher quantities of reaction. The reaction may be accomplished in gram quantities, kilogram quantities, or ton quantities.

In yet a further aspect of the invention, the pyrolytic reaction between the quaternary amine salt and the tetraborohydride is conducted in a single pot. That is, the formation of the polyhedral boranes is conducted in a single vessel without the need for isolation of intermediates or for transferring the reactants to a different vessel. This aspect provides advantages in the yield of the reaction, because no product is lost in isolation, it also facilitates the automation of a process which otherwise involves a number of different steps. In a preferred embodiment, the quench step is performed in the same vessel as the pyrolytic reaction.

In yet a further aspect of the invention, the reaction is anhydrous. By anhydrous it is meant that the components of the reaction (which include the reactants, any additional solvents, and the gasses that the reaction is conducted under) are substantially free of water. As used herein, a liquid is anhydrous when the total water content of the liquid is less than 0.01%. As used herein, solids are anhydrous when the weight of the solid is less than 0.01% water. For a gas to be anhydrous, the water content of the gas is less than 5 ppm.

I. Reaction Parameters

One substrate for the formation of the polyhedral boranes is a tetraborohydride. Tetraborohydrides are safe to handle and readily available. Tetraborohydrides are compounds comprising the $BH_4^-$ anion. The compounds are typically stabilized by a cation ($M^+$). Cations may be chosen from, without limitation, Lithium ($Li^+$), Potassium ($K^+$), Sodium ($Na^+$), and the like. The tetraborohydride provided to the reaction vessel may be anhydrous.

The tetraborohydride reagent is reacted with a quaternary amine salt of the Formula (I). The quaternary amine salt comprises four substituents ($L_{1-4}$) on the nitrogen atom. In some embodiments, $L_{1-4}$ are independently selected from hydrocarbyl and substituted hydrocarbyl having from 1 to 20 carbon atoms. In other embodiments, $L_{1-4}$ are independently selected from hydrocarbyl groups having from 1 to 6 carbon atoms. In another embodiment, $L_{1-4}$ are independently chosen from methyl, ethyl, propyl, and butyl. In an exemplary embodiment, $L_{1-4}$ are ethyl.

Formula (I)

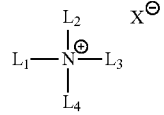

The positively charged quaternary amine is stabilized by an anion to form the salt. The anion ($X^-$) may be any acceptable anion. In some embodiments, the stabilizing ion is chosen from $F^-$, $Cl^-$, $Br^-$, $I^-$, and $OH^-$. In a preferred embodiment, the stabilizing ion is $Cl^-$, and the quaternary amine salt is tetraethyl ammonium chloride.

The quaternary amine salt is provided to the reaction vessel in an anhydrous state. The anhydrous quaternary amine salt may be dried by any known technique for drying the quaternary amine salt. In a preferred embodiment, the quaternary amine salt is dried by placing the quaternary amine salt in a negative pressure environment, which facilitates evaporation and removal of water. Once dried, the quaternary ammonium salt is kept free from water and ambient air; preferably, it is kept under an inert atmosphere such as Argon or Nitrogen. For example, prior to adding any other reagents including, but not limited to, the tetraborohydride, the quaternary amine salt may be dried in the reactor by operating the reactor containing the quaternary amine salt under vacuum at a temperature of about 125° C. and then cooling the dried quaternary amine salt.

The mole-to-mole ratio of the tetraborohydride and the quaternary amine salt can and will vary within the ranges defined herein. The ratio of tetraborohydride to the quaternary amine salt may vary between about 1:0.1 to about 1:5. In another embodiment, the mole-to-mole ratio of the tetraborohydride to the quaternary amine salt may vary between about 1:0.8 to about 1.2, more preferably in a ratio of about 1:1 to about 1:2. In other embodiments, the ratio of the tetraborohydride to the quaternary amine salt may range between about 1:0.8 to about 1:1, between about 1:0.9 to about 1:1.1, between about 1:0.9 to about 1:1.2, between about 1.1 to about 1.2, between about 1:1.3 to about 1:1.3, between about 1:1.3 to about 1:1.5, and between about 1:1.4 to about 1:1.5. In an exemplary embodiment, the ratio of the tetraborohydride to the quaternary amine salt is about 1:1.

In some aspects of the invention, an optional catalyst is added to the reaction between the quaternary amine salt and the tetraborohydride. The optional catalyst is preferably a Lewis acid such as boron trifluoride, trimethoxyboron, or aluminum chloride. The optional catalyst may be added to the reaction in a ratio of about 0.1 to about 5 mol % of the tetraborohydride reagent. In another embodiment, the amount of optional catalyst is about 0.1 to about 0.7 mol % of the tetraborohydride reagent. In yet another embodiment, the amount of Lewis acid catalyst is about 0.5 mol % of the tetraborohydride reagent.

The reaction may further comprise an optional anhydrous solvent. Anhydrous solvents may be obtained commercially or may be dried through various drying mechanisms such as reaction with sodium, use of a drying agent, water scavengers, or another technique known in the art. Solvents include both polar solvents and non-polar solvents. Non-limiting examples of specific polar organic solvents include acetonitrile, acetic acid, acetone, allyl alcohol, butyl acetate, n-butanol, chlorobenzene, chloromethane, cyclopentane, dichloromethane (DCM), dichloroethane, dimethyl sulfonic acid (DMSO), ethanol, ethyl acetate, ethylene dichloride, ethylene bromide, fluorobenzene, formic acid, isobutylmethylketone, isopropanol, isopropyl acetate, methanol, methylene bromide, methylene chloride, methyl iodide, methylethylketone, methyltetrahydrofuran, pentyl acetate, n-propanol, n-propyl acetate, tetrahydrofuran, tetrachloroethane, trichloroethane, water, and the like. Non-limiting examples of specific non-polar organic solvents include benzene, chloroform cyclohexane, cyclopentane, diethyl ether, dioxane, heptane, hexane, pentane, toluene, xylene and the like.

In some aspects of the invention, a high boiling solvent is preferred. Non-limiting examples of high boiling solvents are bis(2-methoxyethyl)ether, 1,2-dimethoxyethane, N,N-dimethylformamide, dimethylsulfoxide, decane, dodecane, hexalin, decalin, tetralin, mixed dimethyl succinate, triesters of 1,2,4-benzenetricarboxylic acid, mineral oils and mixtures thereof.

In embodiments where a solvent is present, the solvent can be provided in a range of acceptable amounts. The amount of solvent used depends on the amount of tetraborohydride reagent and the size of the reactor. In some aspects of the invention the solvent will be provided in a v/v with the substrates of about 10% to about 200%. In some embodiments, the solvent is provided in a v/v of about 50% to about 100%. In still another embodiment the solvent is provided in a v/v of about 20% to about 50%.

The reaction temperature may vary over the course of the reaction. Depending on the size of the reaction, heating to the reaction temperature may occur over a period of time, generally from 0.5 hours to about 3 hours. In a preferred embodiment, the reaction temperature will be reached after about 90 minutes. The reaction temperature for the pyrolysis of a tetraborohydride and a quaternary amine salt may range between about 150° C. and about 300° C. In one embodiment, the reaction is carried out at a temperature ranging between about 160° C. and about 200° C. In another embodiment, the temperature ranges between about 170° C. and about 190° C., between about 185° C. and about 205° C., between about 200° C. and about 220° C., between about 215° C. and about 235° C., between about 230° C. and about 250° C., between about 245° C. and about 270° C., and between about 265° C. and about 300° C. In some embodiments, the temperature may be kept at any temperature between or including the above-listed values. In an exemplary embodiment, where the quaternary amine salt is tetraethyl ammonium chloride, the reaction is conducted between about 180° C. and about 190° C.

During the course of the reaction the pressure of the reaction is regulated, for example, by the reactor described in Part II. Over the pyrolytic process, hydrogen gas is produced which increases the pressure of the vessel. The gas generally is released to maintain the pressure, for example, as described in Part II. The pressure during the reaction may vary throughout the reaction between about 0.2 atm and between about 8 atm. In one embodiment, the pressure is regulated between about 0.4 atm and about 3.0 atm. In a preferred embodiment, the pressure is regulated between about 0.5 atm and about 2 atm.

The pyrolytic reaction between the quaternary amine salt and the tetraborohydride is conducted under anhydrous conditions. Anhydrous conditions are maintained through drying of the reagents before introduction into the reaction vessel, and maintenance of an inert atmosphere within the reaction vessel. Because the reaction vessel is preferably opened to vent, and the vents are preferably configured such that ambient air cannot enter the reaction vessel. An example of such a configuration is provided in Part II.

The amount of time that the tetraborohydride and the quaternary amine salt are allowed to react may depend on whether the process is being optimized for $[B_{10}H_{10}]^{2-}$ or $[B_{12}H_{12}]^{2-}$ and on the temperature of the reaction. Generally, the reaction temperature is held for a period of time ranging from about 4 hours to about 24 hours. In one embodiment, the reaction temperature is held for a period of time from about 10 hours to about 20 hours. In yet another embodiment, the peak temperature is held from about 3 hours to about 6 hours to optimize the process for $[B_{10}H_{10}]^{2-}$. In another embodiment, the peak temperature is held from about 8 hours to about 20 hours to optimize the reaction for $[B_{12}H_{12}]^{2-}$.

After the reaction vessel has cooled to a temperature ranging from about 80° C. and about 120° C., the reaction is preferably quenched to destroy any reactive intermediates in the reaction vessel. The reaction of the tetraborohydride with the quaternary ammonium salt may be quenched by adding a quench reagent to the reaction vessel. The intermediates are highly reactive, thus quenching occurs almost immediately to the introduction of the quench solution. Due to the fact that some of the reactive intermediates may explode on contact with air, it is preferable to introduce the quench reagent to the reaction vessel through an air free mechanism.

Quench reagents are preferably reagents that react with unwanted borohydride intermediates (such as hydrolytically unstable intermediates) and do not react with the desired polyhedral boranes. The quench reagent can be acids or bases as long as they react with the hydrolytically unstable borohydride intermediates. Preferably, the quench reagent is a weak acid or base. Non-limiting examples include acetic acid, alkyl amines, ammonia, formic acid, hydrofluoric acid, hydrocyanic acid, oxalic acid, and pyridine. In a preferred embodiment, the quench reagent is acetic acid.

Facilitating contact of the quench reagent with the reactive boranes can be accomplished by providing agitation of the vessels contents with a liquid quench reagent. Agitation should be sufficient to cause contact with the entire vessel and may be provided by rotation of the vessel, stirring, and the like. In a preferred embodiment, the quench reagent is volatile and added to the reaction vessel above the boiling point of the quench reagent. This causes vaporization of the quench reagent and, facilitates the quench reagent contacting the reactive species in the vessel.

The method of producing the polyhedral boranes may further comprise a purification step to isolate the desired product. The unpurified reaction mixture may comprise $[B_{10}H_{10}]^{2-}$ and/or $[B_{12}H_{12}]^{2-}$, including salts and complexes thereof, as well as a large amount of salt.

The salt is comprised of the stabilizing counterions for the quaternary ammonium salt and for the tetraborohydride (MX) as depicted in Reaction Scheme 1. Purification from this salt may be provided by any known method such as through chromatography, or vacuum drying.

Preferably, $[B_{10}H_{10}]^{2-}$, $[B_{12}H_{12}]^{2-}$, and the salt (MX) are also separated $[B_{10}H_{10}]^{2-}$, $[B_{12}H_{12}]^{2-}$, and the salt (MX) may be separated by chromatography or through distillation. More preferably, $[B_{10}H_{10}]^{2-}$, $[B_{12}H_{12}]^{2-}$, and the salt (MX) are separated based on their differential solubility in alcohol. Another surprising aspect of the invention is that the $[B_{10}H_{10}]N(Et_4)_2$ and $[B_{12}H_{12}]N(Et_4)_2$ may be separated based on differential solubility in methanol. The mixture is washed with methanol, which selectively solubilizes $[B_{10}H_{10}]N(Et_4)_2$. Evaporation of methanol gives the pure $[B_{10}H_{10}]N(Et_4)_2$. The remaining mixture of the salt (MX) and $[B_{12}H_{12}]N(Et_4)_2$ is separated based on differential solubility in acetonitrile, or another like solvent. Other $[B_{10}H_{10}]^{2-}$ and $[B_{12}H_{12}]^{2-}$ may be separated from each other through differential solubility in lower alcohols such as methanol, ethanol, propanol, allyl alcohol, and butanol. Once the polyhedral boranes are separated, the salt (MX) may be separated using a variety of organic solvents.

The yield of the polyhedral boranes will vary. When the process is optimized for $[B_{10}H_{10}]^{2-}$, the yield of $[B_{10}H_{10}]^{2-}$ may be at least about 50%. In one embodiment, the yield of $[B_{10}H_{10}]^{2-}$ may range between about 35% and about 45%. In another embodiment, the yield of $[B_{10}H_{10}]^{2-}$ may range between about 40% and about 50%. In still another embodiment, the yield of $[B_{10}H_{10}]^{2-}$ may be greater than about 50%. When the process is optimized for $[B_{12}H_{12}]^{2-}$, the yield of for $[B_{12}H_{12}]^{2-}$ may be at least about 50%. In another embodiment, the yield of for $[B_{12}H_{12}]^{2-}$ may range between about 40% and about 50%. In still another embodiment, the yield of for $[B_{12}H_{12}]^{2-}$ may be greater than about 50%.

II. Milling Reactor System

The pyrolytic process described herein above may be carried out in a milling reactor system. The milling reactor system may include a sealed reaction vessel in which the pyrolytic process is carried out at a regulated temperature and pressure under anhydrous conditions as described above. Throughout the pyrolytic process, the reaction vessel may rotate in order to intimately admix the reactants using a method similar to that used in existing ball-mill devices. This admixing process may be further enhanced by the inclusion of particulate grinding media within the reaction vessel along with the tetraborohydride and the quaternary amine salt reagents of the pyrolytic reaction. Using the milling reactor, the pyrolytic process may be carried out using all solid-phase reagents, or any combination of solid-phase, liquid phase, and vapor phase reactants.

Referring to FIG. 1, the milling reactor system 100 comprises a reaction vessel 102 within which the reagents of the pyrolytic reaction, an inert gas, and an amount of grinding media may be placed to conduct the pyrolytic process. In addition, the polyhedral borane products may be removed at the conclusion of the pyrolytic process from the reaction vessel 102. The reaction vessel 102 may be rotated by torque supplied by a power drive system 104 in order continuously mix the contents of the reaction chamber during the pyrolytic process.

The milling reactor system 100 may conduct the pyrolytic process under controlled temperature and pressure conditions. The reaction vessel 102 may be heated and/or cooled during the pyrolytic process by a temperature control system 106 in order to maintain the temperature of the contents of the reaction vessel 102 within the range of temperatures defined herein above. Because the reaction vessel 102 is typically operated under sealed conditions, the pressure within the reaction vessel 102 may be maintained by a pressure regulation system 108 to within the pressure range described herein above.

In addition to controlling the pressure within the reaction vessel 102, the pressure regulation system 108 may also remove excess gaseous products including, but not limited to, hydrogen gas and other vapor-phase byproducts of the pyrolytic reaction from within the reaction vessel 102. These gaseous products may be captured, reclaimed, or released in a non-explosive and non-toxic form by a waste treatment/reclamation system 110. For example, hydrogen gas produced by the pyrolytic process and vented from the reaction vessel 102 may be combined with an excess of an inert gas by the waste treatment/reclamation system 110, resulting in a non-explosive dilute hydrogen/inert gas mixture that may be released into the surrounding atmosphere.

(a) Milling Reactor

Figure 2:
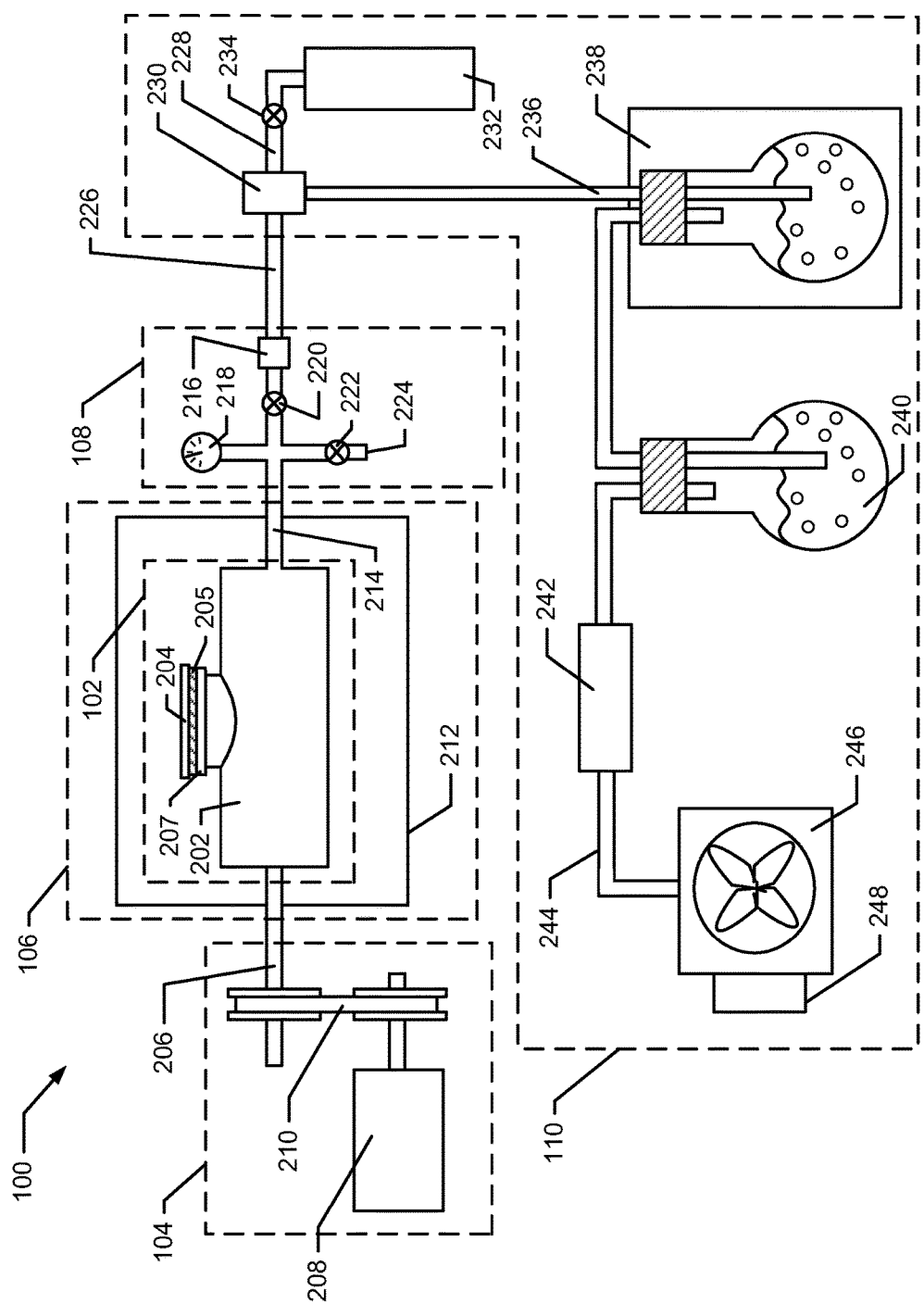
FIG. 2 is a schematic diagram of a milling reactor system.

FIG. 2 is a schematic diagram illustrating an assembly of components making up the milling reactor system 100 in an aspect. The reaction vessel 102 may include a rotating container 202 outfitted with a hatch 204 that may be opened to load in reagents and grinding media for the pyrolytic process and to unload the resulting polyhedral borane products at the completion of the pyrolytic process. Prior to initiating the pyrolytic process, the hatch 204 may be closed and sealed to prevent reactive gases such as air or oxygen from entering the container 202 and to prevent gaseous byproducts such as hydrogen gas from exiting the container 202, thereby reducing the formation or uncontrolled release of explosive byproducts from the pyrolytic process. The hatch may be attached to a flange fitting 207 by any known attachment means capable of reversibly attaching and detaching from the flange fitting 207, including, but not limited to, screws, bolts, and clamps.

The hatch 204 may be sealed using a gasket 205 between the hatch 204 and a flange fitting 207 of the rotating container 202. The gasket 205 may be constructed from any material capable of sealing the hatch at the temperature and pressures of the pyrolytic process described herein above, as well as resisting degradation due to the reactive byproducts of the pyrolytic reaction. In an aspect, a Teflon gasket may be used to seal the hatch 204 to the flange fitting 207.

Any known material or combination of material capable of withstanding the chemical, mechanical and thermal conditions of the pyrolytic process may be used to construct the rotating container 202. The container material may be selected to fulfill any one or more criteria, including, but not limited to: maintaining structural integrity at the pyrolytic process temperatures described above, withstanding the pressures generated during the pyrolysis process, and resisting wear on the interior surfaces of the container 202 due to the impact of the grinding media and/or caustic reagents, byproducts and final products of the pyrolytic process. Non-limiting examples of materials suitable for the construction of the container 202 include plated or stainless steel, such as 304 stainless steel, glass-lined steel, Teflon-lined steel, brass-lined steel, and brass.

Figure 6:
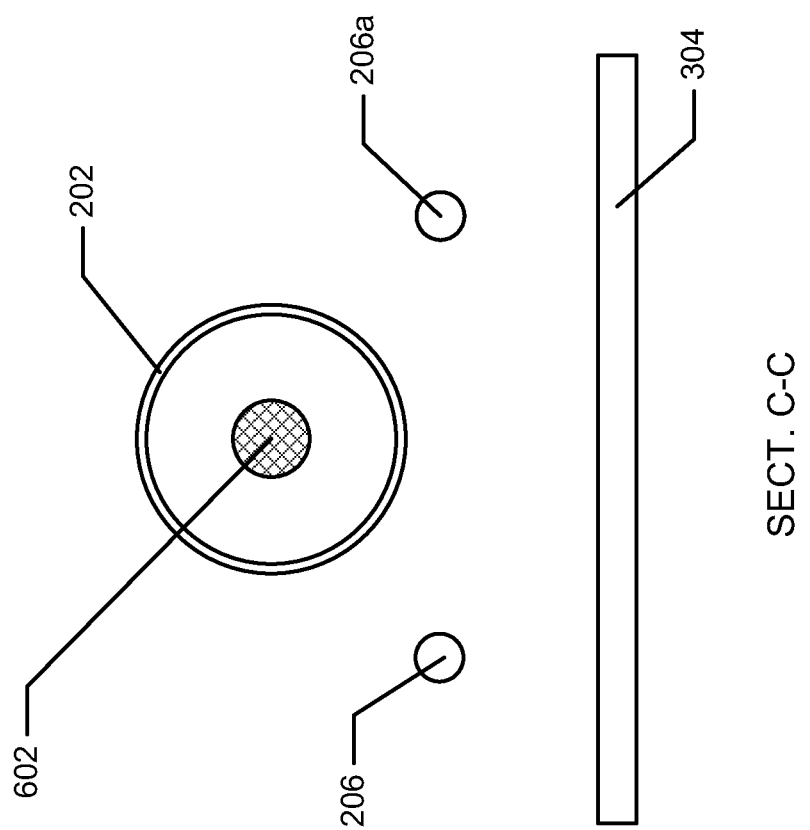
FIG. 6 is a third cross-sectional view of the reaction vessel and power drive system illustrated in FIG. 3.

Grinding media may be introduced into the rotating container 202 prior to the initiation of the pyrolysis process. Any known grinding media may be used, including, but not limited to, balls or spherical particles made of an inert material including, but not limited to, alumina and/or chromium. In an aspect, the grinding media may be made of a catalytic material rather than an inert material, or the grinding material may be an inert material coated with a catalytic material. In an aspect, the grinding media may have a particle diameter of about ⅜ inches. In this aspect, the particle size of the grinding media may be uniform, or a mixture of different particle sizes may be used to enhance the grinding action of the grinding media. FIG. 6 is a cross-section of the rotating container 202 near the gas outlet 214, corresponding to the corss-section marked C-C in FIG. 3. Referring to FIG. 6, a screen 602 may cover the opening within the internal volume of the rotating container 602 in order to prevent the grinding media from exiting the rotating container 202.

Referring back to FIG. 2, the rotating container 202 may be any size appropriate for the production of polyhedral borane products at the desired scale. In an aspect, the size of the rotating container 202 may be determined by any one or more factors including, but not limited to: the desired rate of production of polyhedral borane products, the size of the power drive system 104 and associated structural elements required to support and rotate the rotating container 202, and/or the capacity of the waste treatment/reclamation system 110.

The thickness of the walls of the rotating container 202 may be specified in order to provide sufficient material thickness to compensate for wear induced by the grinding media and chemical erosion during the working life of the rotating container 202. Although the range of internal pressures experienced in the interior of the rotating container 202 are typically relatively low during the pyrolysis process as described herein, if higher internal pressures are desired, the thickness of the walls of the rotating container 202 may be increased accordingly. In an aspect, the container may include a wear-resistant liner to extend the working life of the container 202.

(b) Power Drive System

The power drive system 104 produces and applies the torque needed to rotate the reaction vessel 102 at the desired rotational speed. Referring to FIG. 2, the rotating container 202 may be rotated during the pyrolytic reaction by applying torque generated by a motor 208 through a drive shaft 206 attached to the container 202. The motor 208 may be directly attached to the driveshaft 206, or alternatively the motor 208 may be mechanically engaged with the driveshaft 206 using any known transmissive methods and devices, including, but not limited to, transmission gears and a belt and pulley system 210, as illustrated in FIG. 2.

The motor 208 may be any known motor capable of producing the torque needed to maintain the desired rotation speed of the container 202. Non-limiting examples of suitable motors 208 in include DC electric motors such as permanent-magnet motors, brushed motors, unbrushed motors, and stepper motors; AC electric motors such as synchronous electric motors, induction motors, and shaded pole motors; universal electric motors; pneumatic motors; and hydraulic motors.

The rotation speed of the container 202 induced by the motor 208 may be any rotation speed that results in the mixing of the reagents and grinding media within the container 202. In an aspect, the rotation speed may be specified to fall below a critical rotation speed calculated using Eqn (I):

$$\text{Critical\_Rotation\_Speed} = \frac{76.63}{\sqrt{D}} \quad \text{Eqn. (I)}$$

in which the critical rotation speed is expressed in units of RPM (revolutions per minute) and D is the diameter of the container 202 expressed in units of feet. Without being limited to any particular theory, the critical rotation speed represents the rotational speed at which the contents of the container 202 would be pressed against the inner surface of the container 202 by the centripetal force exerted by the walls. In an aspect, the rotation speed of the container 202 may range from about 65% to about 75% of the critical rotation speed of Eqn (I).

Figure 3:
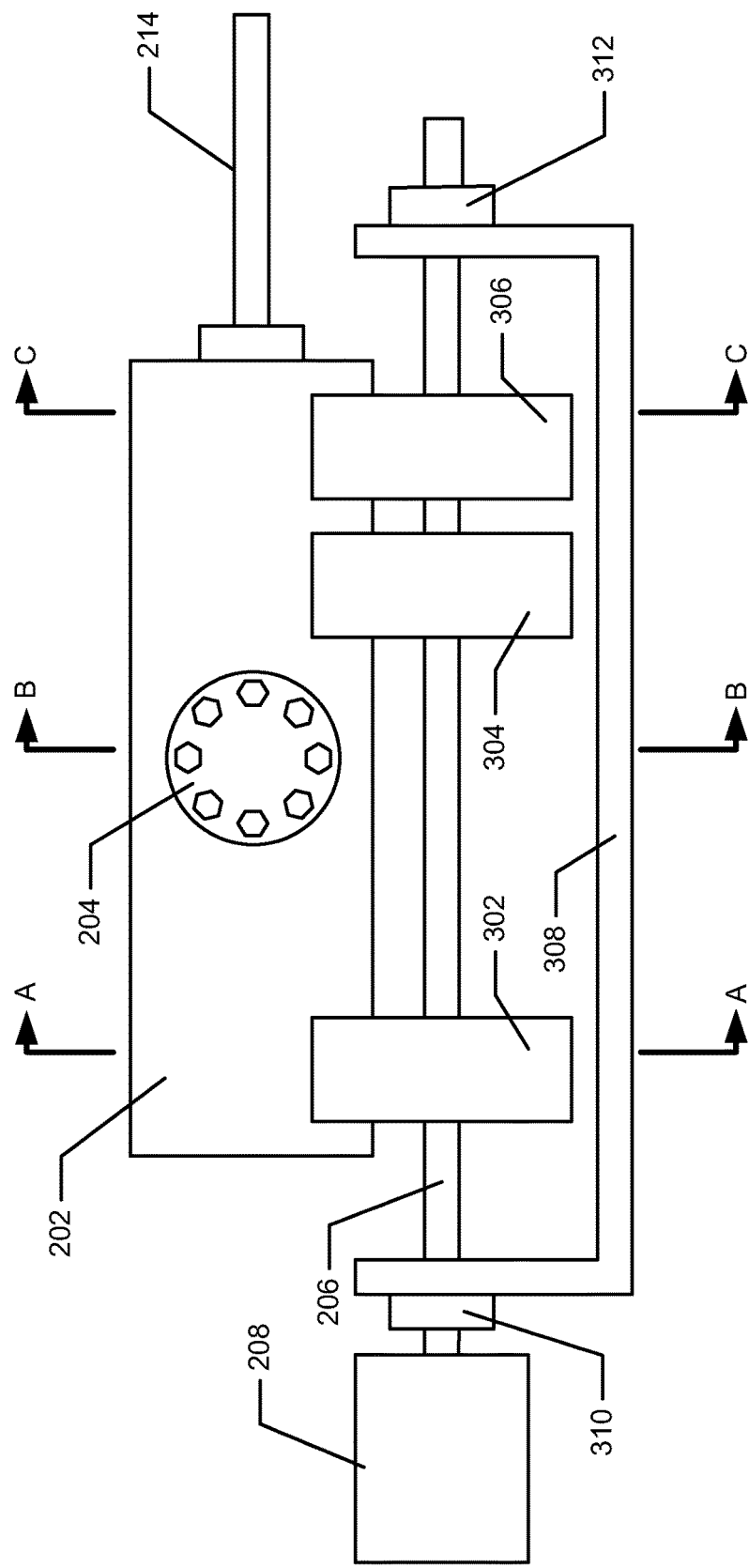
FIG. 3 is a schematic diagram illustrating components of a reaction vessel and a power drive system.

Referring to FIG. 3, the rotating container 202 may be supported by two or more rollers 302, 304, and 206 distributed along the axis of rotation of the rotating container 202. In this aspect, the driveshaft 206 may be attached to each of the rollers 302, 304, and 306 such that the rollers are made to rotate when torque from the engine 208 is applied to the driveshaft 206. The driveshaft may be supported by a pair of bearings 310 and 312 attached to a fixed base 308 that provide a relatively low-friction, rotatable attachment of the driveshaft 206 to the base 308.

Figure 4:
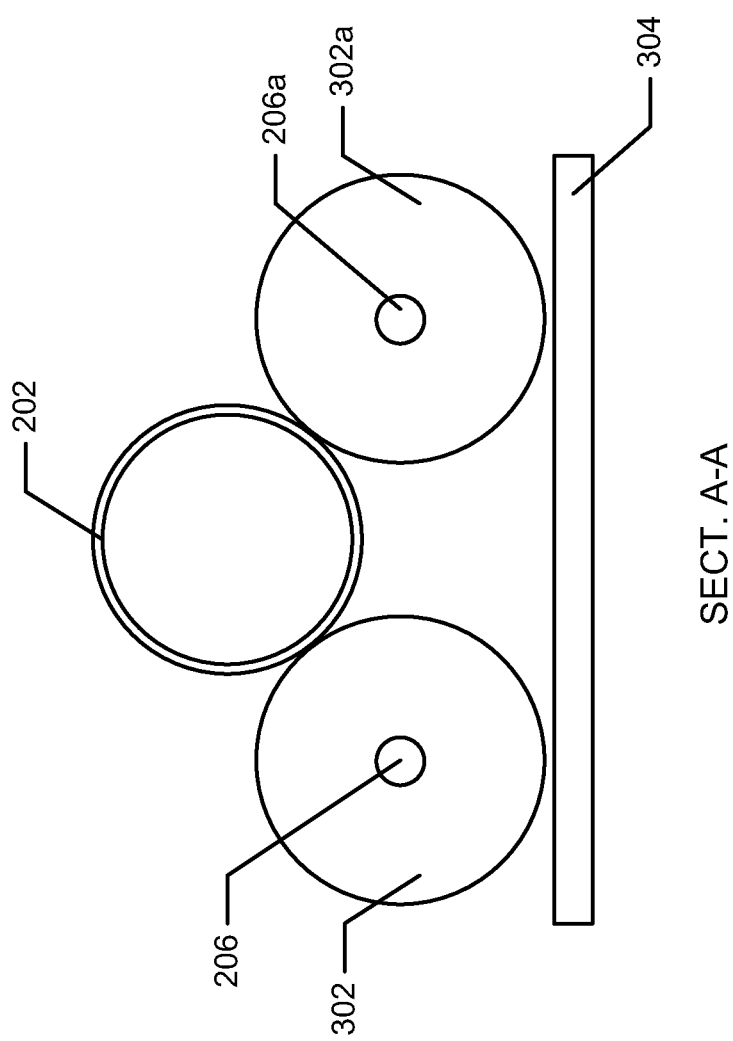
FIG. 4 is a cross-sectional view of the reaction vessel and power drive system illustrated in FIG. 3.

FIG. 4 is a cross-sectional view corresponding to the cross-section marked A-A in FIG. 3. Referring to FIG. 4, the rotating container 202 is supported between the roller 302 and corresponding rear roller 302a. The rear rollers 302a, 304a, and 306a, corresponding to rollers 302, 304, and 306, respectively, are supported on a support shaft 206a attached to the base 304 by means of a second pair of bearings (not shown) similar to the bearings 310 and 312 shown in FIG. 3. In this aspect, the rear rollers 302a, 304a, and 306a rotate passively in reaction to the motion of the rotating container 202 and rollers 302, 304, and 306 in order to provide support against movements lateral to the axis of rotation of the rotating container 202.

Figure 5:
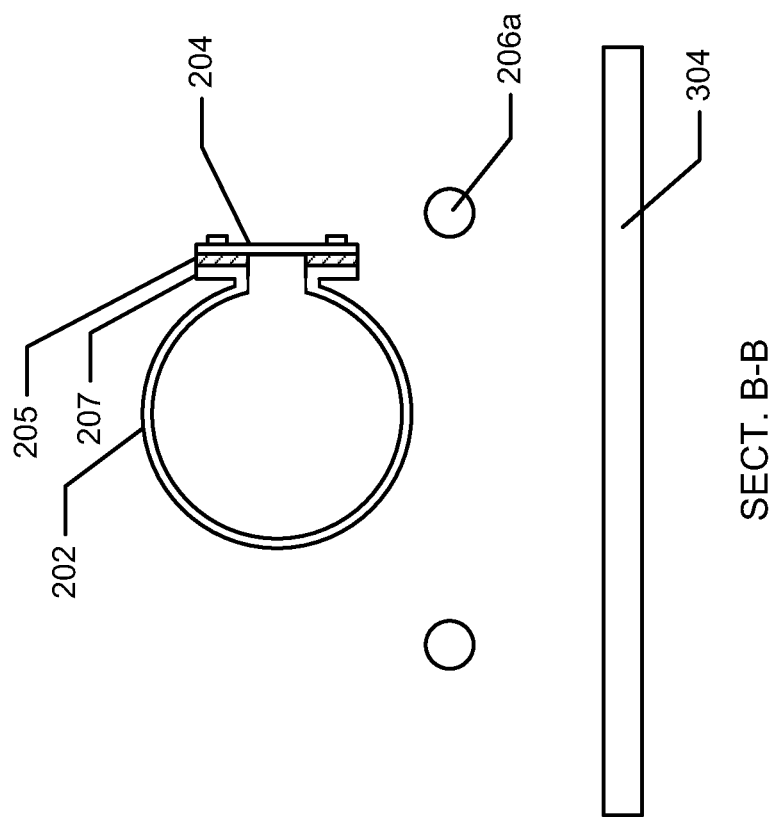
FIG. 5 is a second cross-sectional view of the reaction vessel and power drive system illustrated in FIG. 3.

A cross-section of the supported rotating container 202 through the hatch 204, marked as section B-B in FIG. 3, is illustrated in FIG. 5. Referring to FIG. 5, the rollers 302 and 304 are spaced apart from each other in order to provide space for the hatch 204, gasket 205, and flange fitting 207 to rotate without mechanical interference. The diameter of the rollers 302, 304, and 306 may be specified in part to maintain adequate clearance between the hatch 204, the driveshaft 206, and the support shaft 206a.

(c) Temperature Control System

Referring again to FIG. 2, the temperature control system 106 may include any known heating or cooling device capable of maintaining the rotating container 202 to within a temperature range for the pyrolysis process, as described previously. The temperature control system 106 may consist of a furnace 212 that completely contains the rotating container 202, as illustrated in FIG. 2. Non-limiting examples of heating devices suitable for use in the furnace 212 include resistive electric heaters, inductive heaters, gas heaters, oil heaters, and ceramic heaters. In an aspect, the internal dimensions of the furnace 212 may specified such that the rotating container 202 is completely enclosed within the interior of the furnace 212. In this aspect, the driveshaft 206 and the gas outlet 214 may project from the container to the exterior of the furnace 212 through the side walls of the furnace 212. In an aspect, the walls of the furnace 212 may be insulated in order to maintain a relatively stable temperature within the interior of the furnace 212. In another aspect, the interior of the furnace 212 may be hydraulically sealed in order to maintain an inert atmosphere or a vacuum within the interior of the furnace 212. In yet another aspect, the entire furnace 212 may be situated within a sealed container, including, but not limited to, a glove box. In an additional aspect, the rotating container 202 may be jacketed and heated and/or cooled by the introduction of any known working fluid including, but not limited to, water.

In an aspect, the temperature of the contents of the rotating container 202 may be monitored by any known temperature sensors. In one aspect, the temperature sensor may be a thermocouple temperature sensor situated inside the rotating container 202, and/or attached to the outer surface of the container 202. In another aspect, the temperature may be an infrared temperature sensor situated inside the furnace 212 to monitor the external temperature of the rotating container 202.

(d) Pressure Regulation System

The pressure regulation system 108 regulates the pressure within the rotating container 202 during all phases of the pyrolytic process, and provides a controlled outlet for the gaseous byproducts generated by the pyrolytic process described herein above. Referring to FIG. 2, the rotating container 202 includes a sealed hatch 204 that prevents the entry or escape of gases during the pyrolytic process. During the pyrolytic process, the only pathway by which gaseous products may exit the rotating container 202 is through the reactor gas outlet 214 into the pressure regulation system 108. In one aspect, the rotating container 202 may include a single reactor gas outlet 214, as illustrated in FIG. 2. In another aspect, the rotating container 202 may include two or more reactor gas outlets 214. For example, the rotating container 202 may include two reactor gas outlets attached to opposite ends of the rotating container 202; the two reactor gas outlets may be oriented coincident to the axis of rotation of the rotating container 202.

In another aspect, the reactor gas outlets may also function as conduits through which reactants or other process materials such as quench agent may be introduced into the rotating container 202. In yet another aspect, the rotating container 202 may include one or more nested reactor gas outlets and reactor feed inlets. For example, a reactor gas outlet may be nested inside of a larger reactor feed inlet, and the nested conduits may be attached to one end of the rotating container 202 and oriented coincident to the container's axis of rotation.

As shown in FIG. 2, the pressure regulation system 108 may include a pressure gauge 218, a regulatory pressure valve 220, and a pressure relief valve 222. The pressure gauge 218 may be used to monitor the internal pressure of the rotating container 202. The regulatory pressure valve 220 may be used to control the pressure within the rotating container 202 by allowing gaseous byproducts to exit the rotating container through the regulatory pressure valve 220 when the pressure inside the rotating container 202 exceeds the pressure set point of the regulatory pressure valve 220. A safety release valve 222 is also provided that has a higher set point than the regulatory pressure valve 220, allowing the release of gaseous byproducts through the emergency release vent 224 in the case of a failure of the regulatory pressure valve 220.

In an aspect, the seals and valves of the pressure regulation system 108 are situated outside of the furnace 212 of thermal regulation system 106. Because the pressure regulation system is not subjected to the elevated temperatures inside the furnace, the seals and valves need not be designed and constructed to withstand these elevated temperatures. As a result, a wider range of seal and valve materials and designs may be utilized due to the removal of the elevated temperature conditions.

The regulatory pressure valve 220 may be any known pressure valve having a set point corresponding to the desired internal pressure of the rotating container 202 during the pyrolysis process. In one aspect, the regulatory pressure valve 220 may have a single set point that may be mechanically set prior to the initiation of the pyrolysis process, and maintains this single set point throughout the pyrolysis process. In another aspect, the regulatory pressure valve 220 may be capable of dynamically adjusting the set point during the pyrolysis process in order to vary the internal pressure of the rotating container 202 according to a preset schedule or as a function of some other measured factor such as temperature or composition of the contents of the rotating container 202 in order to produce a desired polyhedral borane product. The materials from which the regulatory pressure valve 220 is constructed may be selected to be resistant to thermal or chemical degradation by the conditions or gaseous byproducts of the pyrolysis process. In an aspect, the regulatory pressure valve 220 may be a poppet-and-spring-type valve constructed out of a durable material selected from stainless steel or brass.

The pressure relief valve 222 may be any known pressure valve having a set point corresponding to the maximum acceptable pressure within the rotating container 202 during the pyrolysis process. Typically, the set point of the pressure relief valve 222 may be specified to be considerably higher than the set point of the regulatory pressure valve 220. In an aspect, the set point of the pressure relief valve 222 is specified in order to avoid rupture of the walls of the rotating container 202, connecting pipes, or seals during the pyrolysis process. The materials from which the pressure relief valve 222 is constructed may be selected to be resistant to thermal or chemical degradation by the conditions or gaseous byproducts of the pyrolysis process. In an aspect, the pressure relief valve 222 may be a poppet-and-spring-type valve constructed out of a durable material selected from stainless steel or brass similar to the regulatory pressure valve 220.

In use, the components of the pressure regulation system 108 may rotate along with the rotating container 202 because of the fixed attachment of the gas outlet 214 to the rotating container 202. In order to simplify the construction of the waste treatment/reclamation system 110 situated downstream relative to the pressure regulation system 108, at least one rotating fitting 218 may be used to connect the waste treatment/reclamation system 110 to the rotating container 202 and associated pressure regulation system 108. The rotating fitting 218 may be located anywhere along the reactor gas outlet 214, the inert gas inlet 226 or any other suitable location that results in the rotation of the rotating container 202 without interfering with the operation of any of the systems of the rotating reactor system 100. Any known rotating connection device may be used as a rotating connector 216, so long as the rotating connector 216 is capable of maintaining an intact, leak-free connection during extended exposure to the gaseous byproducts of the pyrolysis reaction. In an aspect, the rotating connector 216 may include a pair of nested tubes with a relatively low-friction gasket made of a material such as Teflon or other fluorinated polymer materials between the contacting surfaces of the nested tubes.

In general, the connections between all gas-carrying components may be designed to resist the degradative effects of the gaseous byproducts of the pyrolysis process. Any known pressure-tight connection devices may be used, including, but not limited to, threaded stainless-steel fittings with Teflon tape situated between the mating threads of the fittings; flanged fittings sealed with gaskets constructed from Teflon or copper; and any other known connection device capable of withstanding the chemical, thermal, and pressure conditions of the pyrolytic process.

(e) Waste Treatment/Reclamation System

The waste treatment/reclamation system 110 receives the gaseous byproducts from the pyrolysis process and may capture the byproducts, reclaim the byproducts for repeated use, or release the byproducts in a non-explosive and non-toxic form. Referring to FIG. 2, the waste treatment/reclamation system 110 may include a mixing chamber 230 that receives the gaseous byproducts via the reactor gas outlet 226 and an inert gas via an inert gas inlet 288 attached to an inert gas source 232 such as a gas storage tank. The inert gas and gaseous byproducts may enter the mixing chamber 230 resulting in the dilution of the gaseous byproducts by the inert gas. The diluted gaseous byproducts may exit the mixing chamber 230 via the mixing chamber outlet 236. The degree of dilution of the gaseous byproducts may depend upon the flow rate of the gaseous byproducts relative to the flow rate of the inert gas into the mixing chamber 230. For example, a relatively high inert gas flow rate and a relatively low gaseous byproduct flow rate into the mixing chamber 230 results in highly diluted gaseous byproducts exiting the mixing chamber outlet 236. In one aspect, the gaseous byproducts of the pyrolysis process may include hydrogen gas and an amount of inert gas including, but not limited to, nitrogen gas may be mixed with the gaseous byproducts in the mixing chamber 230, resulting in the reduction of the hydrogen concentration in the gaseous byproducts to a sub-explosive concentration. Non-limiting examples of inert gases suitable for use in the mixing chamber 230 include nitrogen, neon, argon, helium, and other noble gases. In another aspect, the flow rate of the inert gas may be controlled by an adjustable valve 234 including, but not limited to, a manually adjustable valve and an actuated valve.

The waste treatment/reclamation system 110 may further include one or more devices to trap and/or filter gaseous byproducts contained within the diluted gas stream exiting the mixing chamber outlet 236. In an aspect, the waste treatment/reclamation system 110 may include a first trap 238 selected from a cryogenic trap or a cold trap as shown in FIG. 2. Without being bound to any particular theory, the first trap 238 may induce the condensation and retention of gaseous components of the waste stream within the first trap 238. In another aspect, the waste treatment/reclamation system 110 may include a second trap 240 and a third trap 242 selected from a cryogenic trap, a cold trap, a condenser, and a filter. The cold trap may include a capture fluid such as a KOH solution to capture gaseous by-products as the waste stream is aerated through the capture fluid. Non-limiting examples of suitable filters include filters containing charcoal, titanium dioxide or other suitable adsorbents and HEPA filters.

In general, any number of filters and/or traps may be included in the waste treatment/reclamation system 110 in any suitable arrangement. For example, two or more traps and/or filters may be arranged in series, as illustrated in FIG. 2. In another example, two or more traps and/or filters may be arranged in parallel. In yet another example, three or more traps and/or filters may be arranged in a combination of series and parallel arrangements. In one such arrangement, two traps arranged in parallel may be placed in series with a filter.

The scrubbed waste stream may emerge from the arrangement of traps and/or filters via a treated waste outlet 244. The treated waste outlet 244 may deliver the treated waste to an exhaust fan 246. The exhaust fan may discharge the scrubbed waste stream to the surrounding atmosphere via a discharge duct 248. Any known explosion-proof fan may be suitable for use as an exhaust fan 246 including, but not limited to, a high velocity exhaust fan.

(f) Continuous Flow Reactor

In an aspect, the milling reactor system 100 may incorporate a continuous flow reactor 202*a* in place of the rotating container 202. The inclusion of the continuous flow reactor 202*a* provides the capability of carrying out the pyrolytic process described herein above in a continuous fashion, rather than in the batch mode of the rotating container 202. In addition, the inclusion of the continuous flow reactor 202*a* may result in a simplified mechanical design, as described herein below.

Figure 7:
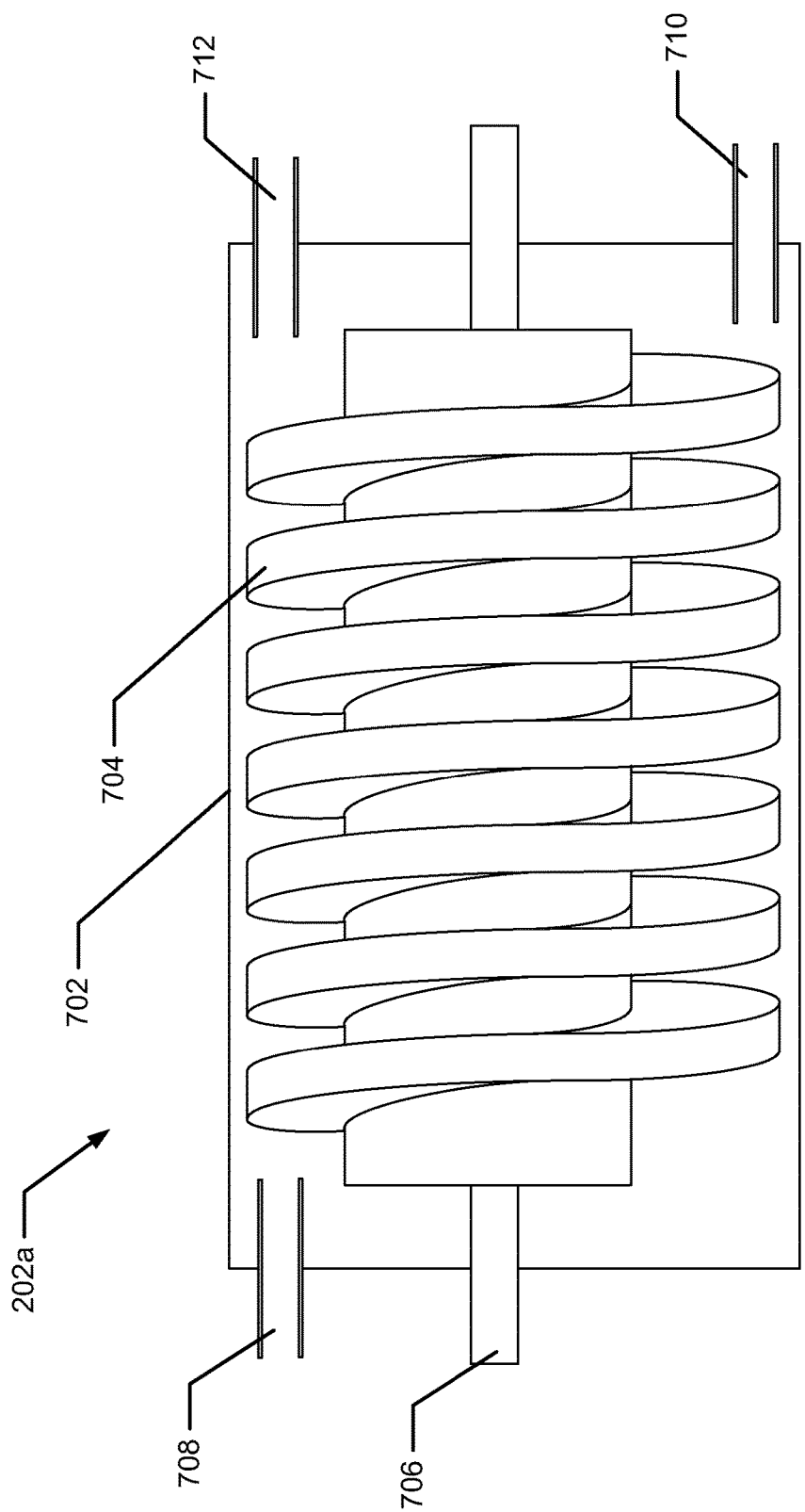
FIG. 7 is a cross-sectional view of a continuous flow reaction vessel.
Figure 8:
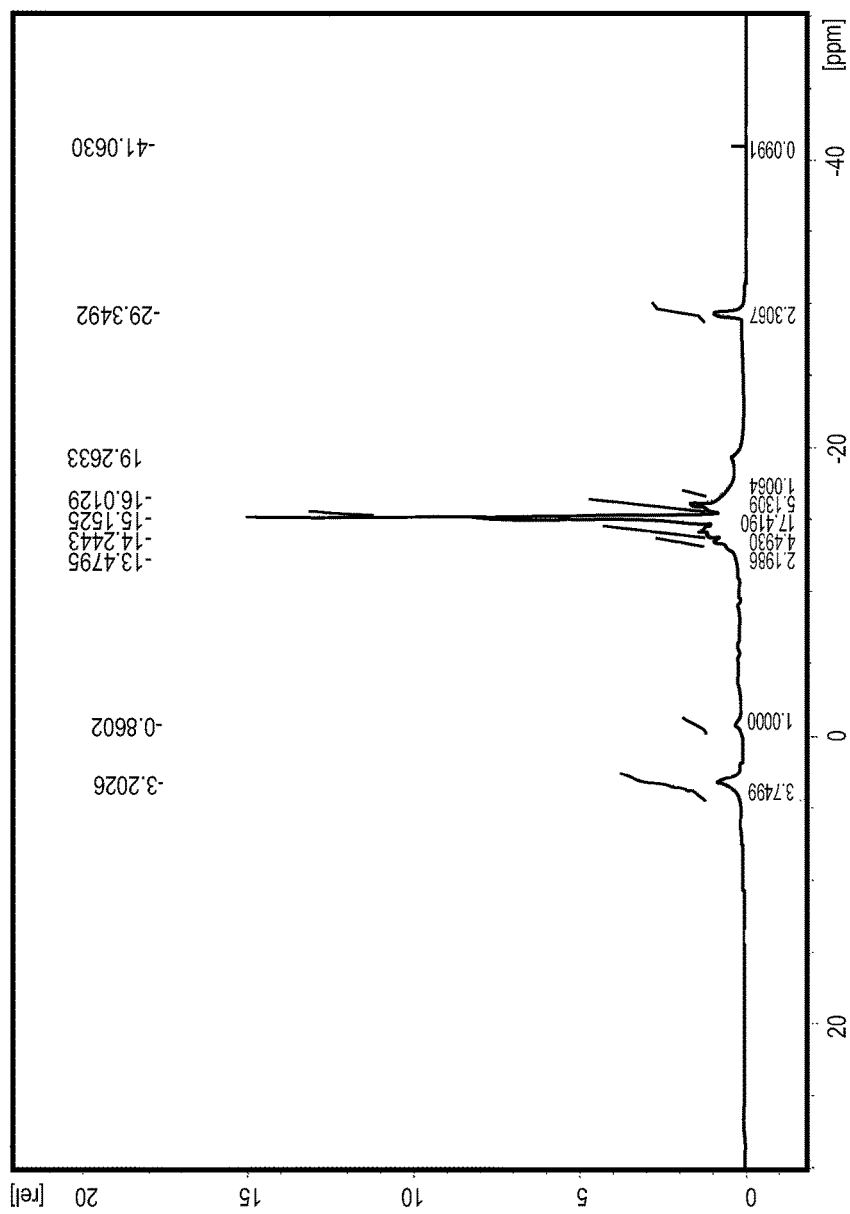
FIG. 8 is an NMR spectrum showing the B-11 NMR chemical shifts associated with $B_{10}H_{10}$. This spectrum includes a signal at −0.8 ppm and one at −29 ppm in a 1:4 ratio. The spectrum shows that the process has minimal side products.
Figure 9:
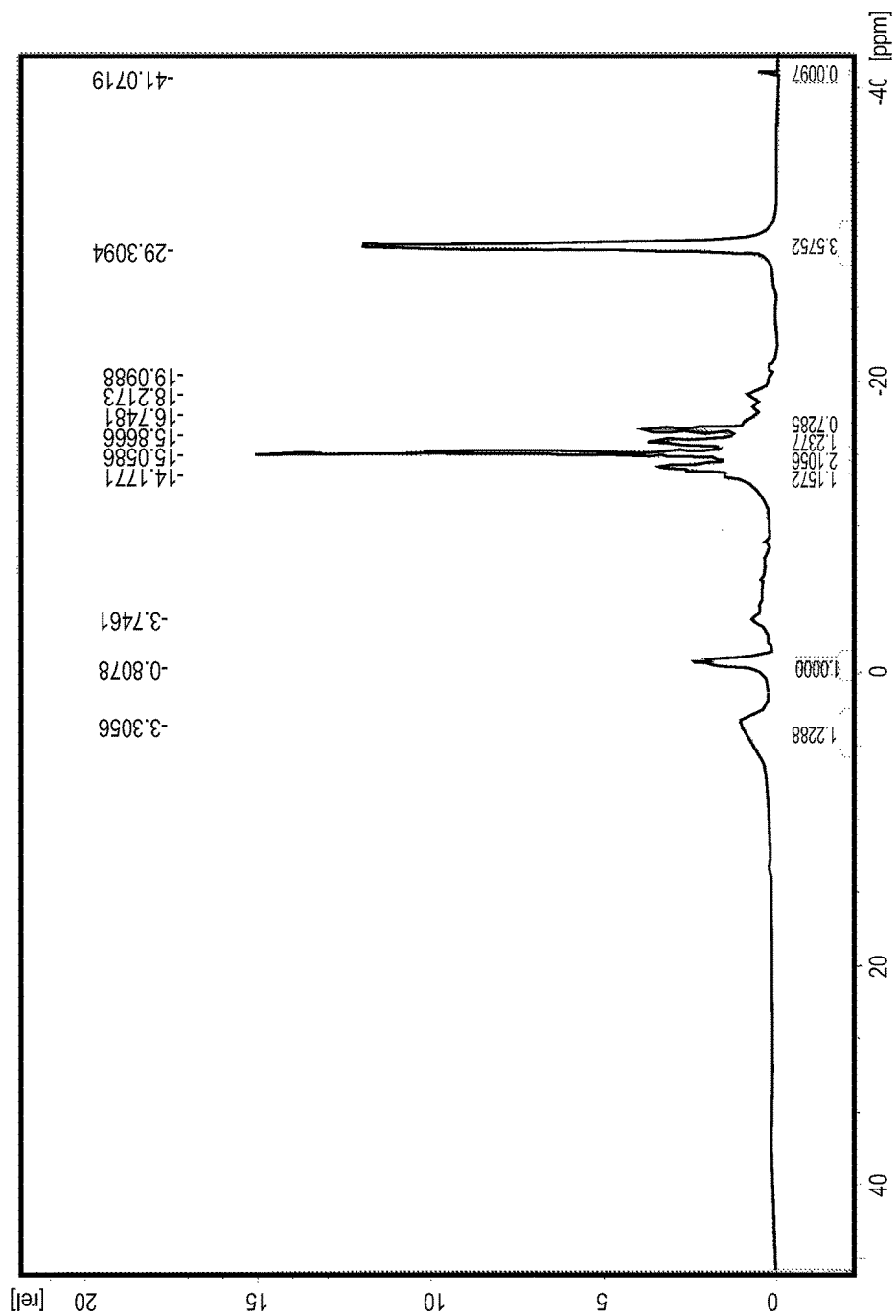
FIG. 9 is an NMR spectrum showing the B-11 NMR chemical shift associated with $B_{12}H_{12}$. This spectrum includes a singlet at −15 ppm. This spectrum confirms that the process results in the production of $B_{12}H_{12}$ with minimal side products.

Referring to FIG. 7, the continuous flow reactor 202A may include a stationary container 702 that is held in a fixed, non-rotating position. The overall length, diameter, and wall thickness of the stationary container 702 may be similarly sized to the corresponding dimensions of the rotating container 202 described herein above. The continuous flow reactor 202A may further include a rotating screw jack 704 that may be situated within the interior space of the stationary container 702 such that the axis of rotation of the screw jack is coincident with the axis of symmetry of the stationary container 702.

A driveshaft 706 may be attached to one end of the screw jack 704 such that the driveshaft 706 extends outward from the screw jack 704 in a direction coincident with the axis of rotation of the screw jack 704. The end of the driveshaft 706 opposite to the screw jack 704 may be operatively connected to the power drive system 104 in a manner similar to the belt and pulley or meshed gear transmissions described herein above. In operation, the screw jack 704 rotates within the stationary container 702, resulting in the mixing of the contents of the continuous flow reactor 202A, as well as a net movement of the contents along the length of the stationary container 702. For example, as shown in FIG. 7, the screw jack 704 may move the contents of the continuous flow reactor 700 from left to right along the length of the stationary container 702. The speed at which the contents of the stationary container 702 move may be governed by any number of factors including, but not limited to, the pitch of the threads of the screw jack 704 and the rotational speed of the screw jack 704.

The stationary container 702 may further contain at least one or more ports that act as conduits into the interior volume of the stationary container 702, including, but not limited to, one or more of: a reactor inlet 708, a reactor outlet 710, and a reactor gas vent outlet 712. The reactor inlet 708 may be used to insert reactant materials, quench agents, and optionally grinding media used in the pyrolytic reactions described herein above. The reactor outlet 710 may be used to remove the polyhedral borane compounds produced using the pyrolysis reaction. The reactor gas vent outlet 712 may be used to vent gaseous by-products including hydrogen out of the stationary container and into the waste treatment/reclamation system 110 as described herein above. Each of the ports may have an associated valve that may be used to open and close the port in the course of conducting the pyrolysis reaction. When all valves associated with all ports are closed, the interior volume of the stationary container 702 is sealed.

In use, the reactants and optional grinding media may be inserted into one end of the stationary container 702 through the reactor inlet 708. These materials may be introduced in any desired manner including but no limited to a continuous feed, a batch feed, and a pulsed feed of two or more discrete batches over a predetermined time period. The rotation of the screw jack 704 may be initiated after the introduction of the reactants and grinding media into the stationary container 702. As the pyrolysis reaction proceeds, the hydrogen gas and other gaseous byproducts produced during the reaction may be vented from the stationary container 702 in order to maintain a desired pressure within the stationary container 702. The reactor gas vent outlet 712 may be connected to the pressure regulation system 108 in order to accomplish suitable control of the internal pressure of the stationary container 702. Propelled by the rotation of the screw jack 704, the polyhedral borane compounds produced by the pyrolysis reaction may be moved to the end of the container opposite to the reactor inlet 708. These polyhedral borane compounds may be removed from the stationary container 702 via the reactor outlet 710.

In an aspect, the incorporation of the continuous flow reactor 202a into the milling reactor system 100 results in a simplified mechanical design compared to the system 100 that includes the rotating container 202. For example, because the stationary container 702 does not rotate during use, no rotary couplings are needed to connect the stationary container 702 to the pressure regulation system 108. In addition, the attachment of sensors such as temperature sensors or pressure sensors to the stationary container 702 may be simplified because the container walls are immobile.

DEFINITIONS

As used herein "alkyl" means hydrocarbyl or substituted hydrocarbyl.

As used herein, "borohydride" means a compound comprising both boron and hydrogen atoms.

As used herein, "hydrocarbon" or "hydrocarbyl" describes organic compounds or radicals consisting exclusively of the elements hydrogen and carbon. These include alkyl moieties. Hydrocarbons or hydrocarbyl may be saturated or unsaturated and may be straight chain, branched, or cyclic.

When introducing elements of the embodiments described herein, the articles "a", "an", "the" and "said" are intended to mean that there are one or more of the elements. The terms "comprising," "including," and "having" are intended to be inclusive and mean that there may be additional elements other than the listed elements.

Having described the invention in detail, it will be apparent that modifications and variations are possible without departing from the scope of the invention defined in the appended claims.

EXAMPLES

Example 1

Production of $B_{10}H_{10}$

One equivalent of tetraethylammonium chloride was placed into a sealed milling reactor. The milling reactor was sealed and the contents of the milling reactor were subjected to vacuum for 5 minutes. An inert gas was added to the reactor in a pressure of about 1 atm. Then about 1 equivalent of sodium borohydride was added to the reactor. The reactor was sealed and allowed to rotate and grind for 5 hours at 200° C. and 0.5 atm. The reaction was quenched with acetic acid.

Example 2

Production of $B_{12}H_{12}$

One equivalent of tetraethylammonium chloride was placed into a sealed milling reactor. The milling reactor was sealed and the contents of the milling reactor were subjected to vacuum for 5 minutes. An inert gas was added to the reactor in a pressure of about 1 atm. Then about 1 equivalent of sodium borohydride was added to the reactor. The reactor was sealed and allowed to rotate and grind for 12 hours at 250° C. and at about 3.5 atm.

What is claimed is:

1. A process for the production of a polyhedral borane in an amount greater than one kilogram, wherein the process comprises a solid-phase, anhydrous, one-pot reaction of a tetraborohydride and a quaternary amine salt under anhydrous pyrolytic reaction conditions without solvent, resulting in the formation of the polyhedral borane.

2. The process of claim 1, wherein the tetraborohydride is chosen from sodium borohydride, potassium borohydride, and lithium borohydride.

3. The process of claim 1, wherein the quaternary amine salt of Formula (I), wherein $L_{1-4}$ are independently chosen from hydrogen, hydrocarbyl, and substituted hydrocarbyl, and $X^-$ is chosen from $F^-$, $Cl^-$, $Br^-$, $I^-$, and $OH^-$

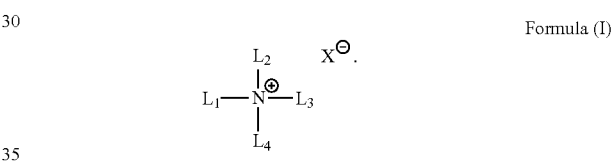

Formula (I)

4. The process of claim 1, wherein the quaternary amine salt is tetraethyl ammonium chloride.

5. The process of claim 1, wherein the pyrolytic conditions comprise a temperature of at least 180° C., and a pressure of at least 0.5 atmospheres.

6. The process of claim 1, wherein the reaction time is at least 5 hours.

7. The process of claim 1, wherein the polyhedral borane is a borane anion.

8. The process of claim 7, wherein the borane anion is $B_{10}H_{10}^{2-}$ or $B_{12}H_{12}^{2-}$.

9. The process of claim 1, wherein the reaction occurs in the presence of a catalyst.

10. The process of claim 9, wherein the catalyst is a Lewis acid in a ratio of about 0.1 to about 5 mol% of the tetraborohydride.

11. The process of claim 1, wherein the tetraborohydride and the quaternary amine salt are present in a ratio between 1:1.3 to 1:1.5.

12. The process of claim 1, wherein $B_{10}H_{10}^{2-}$ is selectively produced in a yield of at least about 40%.

13. The process of claim 1, wherein $B_{12}H_{12}^{2-}$ is selectively produced in a yield of at least about 50%.

14. The process of claim 1, wherein the pyrolytic reaction occurs in a milling reactor.

15. A process for the selective formation of $B_{12}H_{12}^{2-}$ over $B_{10}H_{10}^{2-}$ in an amount greater than one kilogram, the process comprising (a) combining a borohydride with a quaternary amine salt to form an anhydrous reaction mixture; and (b) subjecting the anhydrous reaction mixture to solid-phase, anhydrous pyrolytic reaction conditions without solvent, comprising at least a temperature of 180° C. for at least 12 hours such that the majority of the borohydride is converted to $B_{12}H_{12}^{2-}$.

16. The process of claim 15, further comprising the steps of:
   (a) quenching the pyrolytic reaction with a quench reagent, and
   (b) purifying the resultant reaction mixture to isolate one or more polyhedral boranes.

17. The process of claim 16, wherein the quench reagent is selected from weak acids and bases.

18. The process of claim 17, wherein the quench reagent is acetic acid.

19. The process of claim 16, wherein purification is accomplished by washing the reaction mixture with an alcohol chosen from methanol, ethanol, propanol, allyl alcohol, and butanol.

20. The process of claim 19, wherein the alcohol is methanol.

* * * * *